United States Patent [19]

Horn et al.

[11] Patent Number: 4,935,245
[45] Date of Patent: Jun. 19, 1990

[54] PULVERULENT, WATER-DISPERSIBLE PREPARATION OF A SPARINGLY WATER-SOLUBLE PHARMACEUTICAL ACTIVE COMPOUND AND ITS PREPARATION

[75] Inventors: Dieter Horn, Heidelberg; Reinhard Spengler, Ludwigshafen, both of Fed. Rep. of Germany

[73] Assignee: BASF Aktiengesellschaft, Ludwigshafen, Fed. Rep. of Germany

[21] Appl. No.: 143,074

[22] Filed: Jan. 12, 1988

[30] Foreign Application Priority Data

Jan. 24, 1987 [DE] Fed. Rep. of Germany ....... 3702029

[51] Int. Cl.⁵ .............................................. A61K 9/14
[52] U.S. Cl. .................................... 424/489; 424/499; 424/500; 424/501; 424/502
[58] Field of Search ............... 424/489, 499, 500, 501, 424/502; 252/304, 308, 310, 311, 312; 514/937, 938, 939

[56] References Cited

U.S. PATENT DOCUMENTS

| | | |
|---|---|---|
| 2,885,322 | 5/1959 | Klotz .................................... 424/455 |
| 3,004,892 | 10/1961 | Hainsworth et al. ............... 424/502 |
| 3,147,187 | 9/1964 | Playfair ........................... 424/455 X |
| 4,254,104 | 3/1981 | Suzuki ................... 424/170 |
| 4,522,743 | 6/1985 | Horn et al. ........................... 252/311 |
| 4,695,450 | 9/1987 | Bauer et al. ........................ 424/455 |
| 4,722,838 | 2/1988 | Tocker .................... 424/81 |
| 4,780,316 | 10/1988 | Brox ................................. 424/456 |
| 4,795,643 | 1/1989 | Seth ................... 424/455 X |

FOREIGN PATENT DOCUMENTS

| | | |
|---|---|---|
| 0159237 | 10/1985 | European Pat. Off. . |
| 58-128141 | 7/1983 | Japan .................................. 424/455 |
| 0929227 | 6/1963 | United Kingdom ................ 424/455 |

OTHER PUBLICATIONS

The Indian Journal of Pharmacy, vol. 87, p. 323, 1977
European Search Report.
Lehrbuch der Pharmazeutischen Technologie, Rudolf Voigt, Technol. Verl. Chemie, Weinheim, 5th ed. (1984), 472–474.

Primary Examiner—Thurman K. Page
Attorney, Agent, or Firm—Keil & Weinkauf

[57] ABSTRACT

An aqueous or pulverulent, water-dispersible pharmaceutical preparation which contains an emulsifier, a protective colloid and, in microdisperse form, an edible oil or fat, a sparingly water-soluble active compound being dissolved in the oil or fat, and a process for its preparation.

5 Claims, 1 Drawing Sheet

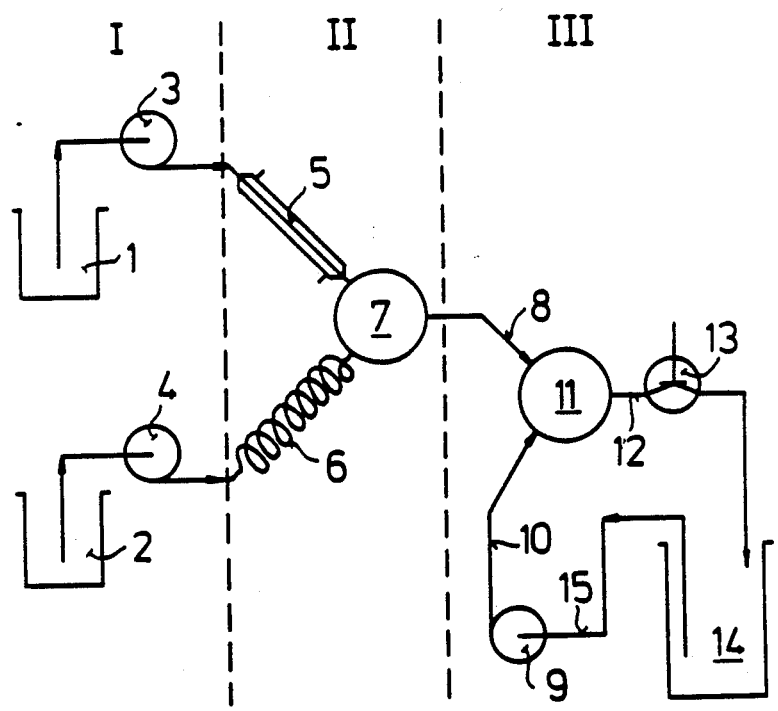

PULVERULENT, WATER-DISPERSIBLE PREPARATION OF A SPARINGLY WATER-SOLUBLE PHARMACEUTICAL ACTIVE COMPOUND AND ITS PREPARATION

The present invention relates to the conversion of hydrophobic, i.e. water-insoluble or sparingly soluble, pharmaceutical active compounds into an aqueous liquid or pulverulent form, the active compound being dissolved in an edible oil or fat, and the oil or fat solution being in the form of very small droplets.

The pharmaceutical formulation of water-insoluble or sparingly soluble pharmaceutical active compounds is always problematic if the active compounds are to be used in water-compatible formulations. To ensure rapid bioabailability of such active compounds, very fine distribution of these compounds is desirable.

Various methods have been described for increasing the absorbability, all of which aim at reducing the size of the crystallites of the active compounds. Most widely used are various milling processes, by means of which the coarsely crystalline synthetic material can be converted to a particle size range of, at best, from 2 to 10 $\mu$m. Although this constitutes an improvement over the initial situation, it is still insufficient in the case of sparingly soluble substances and completely unsatisfactory in the case of virtually insoluble substances, such as the carotenoids. A process described in U.S. Pat. No. 4,522,743 constitutes a certain degree of progress in comparison. Although this process gives an extremely fine distribution of the active compounds, the particle sizes being less than 1 $\mu$m, it still does not provide a molecular disperse distribution. Instead, solid particles are still detectable under the electron microscope.

Molecular disperse distributions in the form of solid solutions were obtained by a very different method in which the active compounds were converted via a melt of a suitable matrix material, such as polyethylene glycols or urea, into a molecular disperse state, from which a solid solution was obtained after cooling, or the active compound, together with a suitable polymer material, such as polyvinylpyrrolidone, was dissolved in a chlorohydrocarbon, the solution was then spray dried and the active compound was thus converted to a molecular disperse solid solution (R. Voigt, Lehrbuch der pharmazeutischen Technologie, Verlag Chemie, Weinheim, 5th Edition, 1984, page 472 et seq.).

However, the last-mentioned processes have considerable disadvantages. In the case of the melt process, heating during the process leads, inter alia, to thermolytic losses of thermally unstable active compounds. Another serious disadvantage of such formulations is that, after the solidified melt has been redissolved in an aqueous system, the active compound frequently recrystallizes, so that the micronization effect initially achieved is eliminated again before biological absorption takes place. It is also observed that recrystallization occurs even in the solidified melt as a result of diffusion of the active compound molecules in the matrix, and the products have only a short shelf life.

The same disadvantages, i.e. recrystallization after redissolution in water and poor shelf life, are also observed in the case of the products obtained by the solution process. This process has the further considerable disadvantage that chlorohydrocarbons have to be used (chloroform, methylene chloride, etc.) in order to meet the requirement for high solubility of both the hydrophobic active compound and the hydrophilic matrix material. Complete removal of the chlorohydrocarbons, which is necessary for toxicological reasons, is technically difficult to achieve.

The biological absorption of active compounds which are sparingly soluble in aqueous media is influenced not only by their fineness but also by endogenous and exogenous effects of the gastrointestinal tract. The endogenous factors (gastrointestinal secretion, peristaltics, pH, biotransformation) are biologically controlled in the absence of pathological changes in the gastrointestinal tract and are thus predetermined and not very variable. On the other hand, exogenous factors which are influenced by the dietary habits of the patient may vary considerably. In the case of sparingly water-soluble, lipophilic active compounds, the fat content of the food consumed together with the drug has an important effect on absorption behavior.

It is an object of the present invention to provide aqueous or pulverulent pharmaceutical preparations which do not have the stated disadvantages but contain the sparingly water-soluble or virtually insoluble active compound in molecular disperse form, and from which, when pulverulent preparations are dissolved in aqueous systems (gastrointestinal tract, infusion solutions), the active compound is liberated in molecular disperse form, so that differences in the fat content of the food consumed together with the drug are unimportant.

We have found that this object is achieved, according to the invention, if the active compound, together with from 2 to 20 times the weight of an edible fat or preferably, oil and an emulsifier is dissolved in a volatile, water-miscible, organic solvent at from 10° to 240° C., preferably from 100° to 200° C., under atmospheric or superatmospheric pressure, the solvent is transferred to the aqueous phase from the resulting molecular disperse solution by mixing with an aqueous solution of a protective colloid at from 0° to 50° C., the oil or fat which contains the active compound in solution forming a microdisperse phase, and the resulting two-phase mixture is freed from the solvent and, where relevant, the water in a conventional manner.

A viscous liquid (oil-in-water emulsion) is obtained, from which the solvent can be removed in a conventional manner, depending on the boiling point, for example by distillation, under atmospheric or reduced pressure, or by extraction with a water-immiscible solvent. Preferably, however, the solvent is removed together with the water by spray drying or spray granulation.

The dry powder thus obtained can be redissolved in water to give a uniform fine distribution of the oily active compound solution having a particle size range of less than 1 $\mu$m.

If necessary, the microdisperse oil or fat phase laden with active compound can also be brought to a suitable pH and then flocculated together with the protective colloid and thus converted to a form from which the solvent and a major part of the water can be separated in a simple manner by filtration or centrifuging. The coacervate thus obtained is then further dried in a conventional manner and converted to granules.

Active compounds which can be used for carrying out the invention have a positive value of the logarithmic n-octanol/water distribution coefficient, log P (A. Leo and C. Hansch, Substituent Constants for Correlation Analysis in Chemistry and Biology, Wiley, New York 1979). Active compounds having a log P value of greater than 1 are preferred.

Water-miscible, heat-stable, volatile solvents containing only carbon, hydrogen and oxygen are particularly suitable for carrying out the novel process, examples being alcohols, ethers, esters, ketones and acetals. Methanol, ethanol, n-propanol, isopropanol, butane-1,2-diol 1 methyl ether, propane-1,2-diol 1-n-propyl ether and acetone are preferably used. In general, it is advantageous to use solvents which are not less than 10% water-miscible, have a boiling point of less than 200° C. and contain less than 7 carbon atoms.

Suitable edible oils or fats are those which are liquid at 50° C., preferably 30° C. Examples are vegetable oils, such as corn oil, olive oil, poppy-seed oil, rape oil, castor oil, coconut oil, sesame oil, Aradisol soybean oil, peanut oil, sunflower oil, palm oil or cottonseed oil. Peanut oil is particularly preferred. Other suitable oils or fats are the fish oils which are rich in eicosapentenoic acid and docosahexenoic acid, as well as neat's foot oil, shortening, beef dripping and butter fat.

Examples of suitable emulsifiers are esters of long-chain fatty acids with ascorbic acid, in particular ascorbyl palmitate, mono- and diglycerides of fatty acids and their oxyethylation products, esters of mono-fatty acid glycerides with acetic acid, citric acid, lactic acid or diacetyltartaric acid, polyglycerol fatty esters (for example the monostearate of triglycerol), sorbitan fatty acid esters, propylene glycol fatty acid esters, 2-(2'-stearoyllactyl)-lactic acid salts and lecithin.

Examples of protective colloids are polypeptides, such as gelatin, casein, caseinate, polysaccharides, such as starch, dextrin, dextran, pectin and gum arabic, as well as whole milk, skimmed milk, milk powder or mixtures of these. However, it is also possible to use polyvinyl alcohol, vinyl polymers, for example polyvinylpyrrolidone, (meth)acrylic acid polymers and copolymers, methylcellulose, carboxymethylcellulose, hydroxypropylcellulose and alginates. For further details, reference may be made to R. A. Morton, Fast Soluble Vitamins, Intern. Encyclopedia of Food and Nutrition, Vol. 9, Pergamon Press 1970, pages 128–131.

To improve the technological properties of the end product, it is advantageous to add to the colloid a plasticizer, such as sugars or sugar alcohols, e.g. sucrose, glucose, lactose, invert sugar, sorbitol, mannitol or glycerol. Minor amounts of, for example, methylparaben, propylparaben, sorbic acid and/or Na benzoate may be added as preservatives.

Other pharmaceutical auxiliaries, such as binders, disintegrating agents, flavor materials, vitamins, colorants, stabilizers, wetting agents and additives which influence the pH (cf. H. Sucker et al., Pharmazeutische Technologie, Thieme-Verlag, Stuttgart 1978), can also be introduced via the solvent or the aqueous phase. For example, in order to increase the stability of the active compound to oxidative degradation, it is often advantageous to use stabilizers, such as α-tocopherol, lecithin, tert-butylhydroxytoluene, tert-butylhydroxyanisole, ethoxyquins or ascorbyl palmitate. They can be added to either the aqueous phase or the solvent phase but are preferably dissolved together with the oil or fat in the solvent phase.

The pharmaceutical preparations obtainable according to the invention contain from 0.5 to 34, preferably from 2 to 20, % by weight of active compound, from 2.5 to 68% by weight of an edible oil or fat, from 5 to 50% by weight of a protective colloid, from 0.1 to 30, preferably from 1 to 10, % by weight of one or more emulsifiers and from 0 to 70% by weight of a plasticizer, with or without minor amounts of stabilizers and with or without other pharmaceutical auxiliaries (up to a total of 60% by weight), all percentages being based on the dry material; the mean particle size of the solution of the active compound in the oil or fat in the form of the powder is less than 0.5 μm. The product contains virtually no oil or fat particles having a particle size greater than 1 μm.

Specifically, the novel process is carried out as follows, for example using an apparatus as shown schematically in FIG. 1.

The apparatus is divided into parts I, II and III. Part II may be the high temperature section, while in parts I and III the temperatures are less than 50° C.

In vessel (1), a suspension of the active compound is initially taken together with the oil or fat in the selected solvent, with or without the addition of from 0.1 to 10% by weight, based on the mixture, of stabilizers. If it is heat-sensitive and sparingly and soluble at room temperature and therefore has to be dissolved rapidly at elevated temperatures, the active compound should be in finely milled form (particle size <50 μm). Vessel (2) contains the solvent without admixed active compound. The suspension of active compound and the solvent are fed to mixing chamber (7) via the pumps (3) and (4) respectively; the mixing ratio can be predetermined by selecting the particular delivery of the pumps and is chosen so that, depending on the solubility of the active compound in the solvent and the desired residence time, the resulting concentration of active compound in the mixing chamber is from 0.5 to 10% by weight, based on the solution. In the case of a heat-sensitive active compound, the volume of the mixing chamber (7) is preferably such that the residence time in (7) is preferably less than 1 second at the selected delivery of the pumps (3) and (4).

Before entering the mixing chamber, the solvent is brought to the desired temperature by means of the heat exchanger (6), while the oil-containing suspension of active compound is kept at below 50° C. by feeding it via the thermally insulated line (5). As a result of turbulent mixing in (7) at from 10° to 240° C., preferably from 100° to 200° C. (in the case of active compounds and oils which are only sparingly soluble at room temperature even in the most suitable solvent), both the active compound and the oil or fat dissolve, and the resulting solution passes via the overflow (8), after a short residence time, preferably less than 1 second in the case of heat-sensitive substances, into the second mixing chamber (11), in which admixing of an aqueous protective colloid/plasticizer solution via the pump (9) and the feed line (10) results in division of the molecular disperse solution of active compound into a two-phase mixture with formation of a microdisperse oil or fat phase containing the active compound in solution and a homogeneous, aqueous phase containing the water-miscible solvent and the protective colloid. The microdisperse two-phase mixture is then discharged via line (12) and the pressure relief valve, and fed to stock vessel (14). To obtain a very high concentration of active compound, the emulsion can be circulated via the suction line (15).

If the pressure relief valve (13) is set at above 1 bar, it is even possible to use solvents at temperatures above their boiling point (under atmospheric pressure) in the novel process.

A pulverulent preparation can be obtained from the emulsion in a conventional manner, for example as described in DE-A No. 25 34 091, by spray drying or by spray cooling or by coating of the particles, isolation and drying in a fluidized bed.

For spray drying, the emulsion is either first freed from the solvent by distillation, preferably under reduced pressure, or by extraction with a water-immiscible solvent, or the entire mixture is spray dried and water and solvent stripped off together in the spray tower in this manner.

The pulverulent active compound is generally obtained in a dry or free-flowing form at the bottom of the spray tower. In some cases, it may be advantageous additionally to carry out complete drying in a fluidized bed.

Instead of preparing the powder formulation by spray drying, it is also possible to use any other methods to convert the active compounds already finely distributed in the water/oil/solvent dispersion into powder form. In a known method which is equally suitable for gel-forming protective colloids and assistants, for example, the O/W emulsion freed from the solvent is emulsified with liquid paraffin to give an O/W/O double emulsion, the mixture is cooled, the liquid paraffin is separated from the gelled particles, and the resulting preparation is washed with naphtha and dried in a fluidized bed.

In the novel procedure, it is particularly surprising that the use of the stated water-miscible solvents mixed with an edible oil or fat and emulsifiers permits the preparation of supersaturated solutions from which, in the microdisperse oil phase after the phase separation induced by the turbulent mixing with the aqueous protective colloid solution, even during removal of the volatile solvent, for example by spray drying, and after cooling, no recrystallization of the active compound occurs within the submicroscopic oil droplets laden (theoretically overladen) with the active compound.

It is also surprising that mixing the solvent-containing oil solution of the active compounds with the aqueous protective colloid solution induces a phase separation in which the disperse oil phase is obtained in the form of extremely small particles, as are scarcely obtainable by mechanical homogenization. This finely divided state of the oil phase laden with active compound is surprisingly retained even during removal of the volatile solvent, for example by spray drying. It is easily possible to obtain preparations in which the major part of the oil phase has a particle size of 0.2 μm without oil particles greater than 1 μm simultaneously being present.

By an appropriate choice of the protective colloid, it is possible to prepare powder preparations whose dissolution properties in aqueous media can be adjusted as desired from rapid solubility in cold water to poor solubility, the oil phase in each case being in the form of submicroscopic, readily absorbable particles. It is even possible to obtain preparations which liberate the microdisperse oil phase only after enzymatic degradation of the protective colloid and under pH control along the intestinal tract.

The Examples which follow illustrate the novel process.

EXAMPLE 1

18 g of 1,7-bis-(3-methoxyphenyl)-3-methylaza-7-cyanononadecane hydrochloride monohydrate (anipamil hydrochloride) were suspended with vigorous stirring, in a solution of 14.5 g of ascorbyl palmitate, together with 73 g of peanut oil in 1 l of isopropanol, the pressure relief valve (13) was set at 25 bar and the said suspension was mixed in the mixing chamber (7) with isopropanol which had been heated to 225° C. in the heat exchanger (6). With the suspension being metered at 2 l/h and the solvent at 3 l/h, the residence time in the mixing chamber (7) was 0.35 second. The molecular disperse solution formed at 190° C. was then fed to the mixing chamber (11), in which turbulent mixing with an aqueous solution of 15 g of gelatine and 22.5 g of sucrose per liter, brought to pH 9 with 1N NaOH, at a metering rate of 27 l/h, resulted in phase separation with formation of a microdisperse oil phase which contained the anipamil in solution. In the collecting vessel (14), a microdisperse two-phase mixture at 50° C. was obtained. Particle size analysis by proton correlation spectroscopy (according to B. Chu, Laser Light Scattering, Academic Press, New York 1974) gave a value of 240 nm for the mean particle diameter of the oil phase and a distribution width of ±40%.

Removal of the solvent under reduced pressure at 50° C. in a distillation apparatus gave a viscous liquid which could be converted to a stable, water-soluble dry powder by spray drying. The anipamil content of this dry powder was 2.4% by weight.

Redissolving the dry powder in cold water gave a solution in which the oil phase was again in the form of a microdisperse phase, the particle size being 310 nm ±40%.

EXAMPLE 2

10 g of 1-(3-methyl-4-nitroimidazol-2-yl)-2-(5-ethyl-1,3,4-thiadiazol-2-yl)-prop-1-ene were suspended in a solution of 8 g of ascorbyl palmitate together with 40 g of peanut oil in 192 g of isopropanol, and micronized in the same manner as in Example 1. The particle size distribution of the oil phase laden with active compound in the micronized material corresponded to that of the micronized material of Example 1.

EXAMPLE 3

5 g of 2'-(2-hydroxy-3-propylaminopropoxy)-3-phenylpropiophenone (propafenone) were suspended in 240 g of a solution of 4 g of the ester of diacetyltartaric acid with mono-fatty acid glyceride together with 20 g of peanut oil in isopropanol and micronized in the same manner as in Example 1. In the micronized material, the mean particle size of the oil phase laden with active compound was 184 nm ±29%.

EXAMPLES 4-19

Micronized materials having the same physicochemical properties as the micronized material from Example 1 were prepared in the same manner as in Example 1, using the active compounds listed in the Table below.

TABLE 1

| Example | Active compound | Mean particle size of the oil phase laden with active compound, in nm |
|---|---|---|
| 4 | (Z)-2-chloro-10-(4-methylpiperazinyl)-5H-dibenzo[a,d]cyclohepten-5-ylidene-acetonitrile (Rilapin) | 273 ± 44% |
| 5 | 11-(4-methylpiperazinylcarbonyl-methylidene)-5,11-dihydro-6H-dibenz[b,e]-azepin-6-one | 339 ± 33% |

TABLE 1-continued

| Example | Active compound | Mean particle size of the oil phase laden with active compound, in nm |
|---|---|---|
| 6 | 1-(3-methyl-4-nitroimidazol-2-yl)-2-(5-ethyl-1,3,4-thiadiazol-2-yl)-prop-1-ene | 362 ± 45% |
| 7 | Z-1-(1,2,4-triazol-1-yl-methyl)-1-(4-chlorophenyl)-2-(2,4-dichlorophenyl)-oxirane | 307 ± 36% |
| 8 | 1-[3-(5-methyl-1,3,4-oxadiazol-2-yl)-phenoxy]-3-[4-(2-methoxyphenyl)-piperazin-1-yl]-propan-2-ol fumarate (Nesapidil) | 286 ± 40% |
| 9 | 3-aza-7-cyano-1,7-bis(3,4-dimethoxyphenyl)-3,8-dimethylnonane (Verapamil) | 300 ± 37% |
| 10 | 3-methylaza-7-cyano-1,7-diphenylnonadecane (Ronipamil) | 240 ± 40% |
| 11 | 1-bicyclo[2.2.1]hept-5-en-2-yl-1-phenyl-3-piperidinylpropan-1-ol (Biperiden) | 260 ± 35% |
| 12 | 2'-(2-hydroxy-3-n-propylaminopropoxy)-3-phenylpropiophenone (Propafenone) | 269 ± 38% |
| 13 | 5,6-dihydro-4-methoxy-6-(2-phenylethenyl)-2H-pyran-2-one (Kawain) | 323 ± 34% |
| 14 | 2-(4-i-butylphenyl)propionic acid (Ibuprofen) | 265 ± 37% |
| 15 | 4-(2-piperidinylhydroxymethyl)-2,8-bis-trifluoromethylquinoline (Mefloquine) | 335 ± 42% |
| 16 | 7-chloro-1,3-dihydro-1-methyl-5-phenyl-2-H-1,4-benzodiazepin-2-one (Diazepam) | 303 ± 45% |
| 17 | 5-amidocarbonyl-5H-dibenz[b,f]azepine (Carbamazepine) | 313 ± 41% |
| 18 | 1,3-bis(2-carboxy-4-oxochromen-5-yl-oxy)-1,3-propan-2-ol, disodium salt (sodium chromoglycate) | 313 ± 40% |
| 19 | 3-amino-N-(2-dimethylaminoethyl)-1,8-naphthalimide (Amonafide) | 286 ± 30% |

We claim:

1. A pulverulent, water-dispersible pharmaceutical preparation which contains an emulsifier, a protective colloid and, in microdisperse form, an edible oil or fat, a sparingly water-soluble active compound being dissolved in the oil or fat.

2. A pulverulent pharmaceutical preparation as defined in claim 1, wherein the active compound has a positive logarithmic octanol/water distribution coefficient.

3. A pulverulent pharmaceutical preparation as defined in claim 2, wherein the logarithmic octanol/water distribution coefficient of the active compound is >1.

4. A pulverulent pharmaceutical preparation as defined in claim 1, wherein the mean diameter of the oil or fat particles is less than 0.5 μm.

5. A pulverulent pharmaceutical preparation as defined in claim 1, which contains the following components in the following amounts, based on the dry material:

from 0.5 to 34% by weight of active compound,
from 2.5 to 68% by weight of an edible oil or fat,
from 5 to 50% by weight of a protective colloid,
from 0.1 to 30% by weight of an emulsifier,
from 0 to 70% by weight of a plasticizer and
from 0 to 60% by weight of one or more conventional pharmaceutical auxiliaries.

* * * * *